(12) United States Patent
Hosier et al.

(10) Patent No.: US 9,888,955 B2
(45) Date of Patent: Feb. 13, 2018

(54) ELECTROSURGICAL SYSTEM AND AN ELECTRODE ASSEMBLY FOR AN ELECTROSURGICAL SYSTEM

(75) Inventors: John Roland Hosier, Cardiff (GB); Michael David Newton, Newport (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 982 days.

(21) Appl. No.: 12/591,054

(22) Filed: Nov. 5, 2009

(65) Prior Publication Data
US 2010/0121320 A1 May 13, 2010

Related U.S. Application Data

(63) Continuation-in-part of application No. 12/153,364, filed on May 16, 2008, now Pat. No. 8,876,816.
(Continued)

(30) Foreign Application Priority Data

May 24, 2007 (GB) .................................. 0709993.0

(51) Int. Cl.
*A61B 18/14* (2006.01)
*A61B 18/12* (2006.01)
(Continued)

(52) U.S. Cl.
CPC .......... *A61B 18/1206* (2013.01); *A61B 18/14* (2013.01); *A61B 90/90* (2016.02);
(Continued)

(58) Field of Classification Search
CPC ................ A61B 18/1206; A61B 18/14; A61B 2018/00178; A61B 2018/00642; A61B 19/44
(Continued)

(56) References Cited

U.S. PATENT DOCUMENTS 4,569,345 A 2/1986 Manes
4,739,759 A 4/1988 Rexroth et al.
(Continued)

FOREIGN PATENT DOCUMENTS

JP 2004-016445 1/2004
WO 93/06776 A 4/1993

OTHER PUBLICATIONS

English Translation of Office Action dated Mar. 23, 2011 in Chinese application No. 200880017169.0.
(Continued)

*Primary Examiner* — Michael Peffley
*Assistant Examiner* — Samantha Good
(74) *Attorney, Agent, or Firm* — Nixon & Vanderhye PC (57) ABSTRACT

An electrosurgical system includes a first unit including a generator, and a second unit including an electrode assembly, the second unit being detachably connectible to the first unit such that radio frequency power can be conveyed to the electrode assembly, wherein the second unit firstly includes a passive electrical identification component having a parameter of a finite non-zero value indicative of a characteristic of the electrode assembly, and the second unit additionally includes an output circuit adapted to generate an identifiable characteristic signal, the first unit firstly including a sensing circuit for determining the value of the electrical identification component so as to identify the second unit when the second unit is connected to the first unit, and the first unit additionally including means for receiving the identifiable characteristic signal from the output circuit when the second unit is connected to the first unit.

7 Claims, 9 Drawing Sheets

Related U.S. Application Data (60) Provisional application No. 60/929,111, filed on Jun. 13, 2007.

(51) Int. Cl.
    *A61B 18/00*     (2006.01)
    *A61B 90/90*     (2016.01)

(52) U.S. Cl.
    CPC ............... *A61B 2018/00178* (2013.01); *A61B 2018/00642* (2013.01)

(58) Field of Classification Search
    USPC ...................................................... 606/32, 34
    See application file for complete search history.

(56) References Cited

U.S. PATENT DOCUMENTS

| | | | |
|---|---|---|---|
| 4,919,508 | A | 4/1990 | Grace et al. |
| 5,697,955 | A | 12/1997 | Stolte |
| 6,074,386 | A | 6/2000 | Goble et al. |
| 8,876,816 | B2 * | 11/2014 | Hosier .............................. 606/34 |
| 2001/0039389 | A1 | 11/2001 | Sakurai et al. |
| 2002/0029036 | A1 | 3/2002 | Goble et al. |
| 2004/0044339 | A1 | 3/2004 | Beller et al. |
| 2004/0054365 | A1 * | 3/2004 | Goble ................ A61B 18/1206 606/34 |
| 2004/0133189 | A1 * | 7/2004 | Sakurai .............................. 606/1 |

OTHER PUBLICATIONS

Office Action issued in pending U.S. Appl. No. 12/153,364, dated Aug. 9, 2011.

International Search Report issued in corresponding PCT Application PCT/GB2008/001719, dated Oct. 27, 2008.

Search Report issued in U.S. Priority Application No. GB0709993.0 (Date of Search: Sep. 19, 2007).

Patent Examination Report No. 1 in corresponding Australian Application No. 2008252650, dated Aug. 14, 2012.

Patent Examination Report No. 1 in corresponding Japanese Application No. 2010-508897, dated Dec. 12, 2012.

English translation of Patent Examination Report No. 1 in corresponding Japanese Application No. 2010-508897, dated Dec. 21, 2012.

Computer English Translation of JP Application No. JP2004-016445, dated Jan. 22, 2004.

English Abstract of Japanese Application No. JP2004-016445, Jan. 22, 2004.

Search Report issued in corresponding Canadian Application No. 2,686,426, dated Nov. 5, 2014.

Office Action issued in corresponding Canadian Application No. 2,686,426, dated Nov. 14, 2014.

Office Action issued in corresponding Canadian Application No. 2,686,426, dated Jul. 20, 2015.

\* cited by examiner

ELECTROSURGICAL SYSTEM AND AN ELECTRODE ASSEMBLY FOR AN ELECTROSURGICAL SYSTEM

CROSS-REFERENCES TO RELATED APPLICATIONS

This application is a continuation-in-part of application Ser. No. 12/153,364, filed May 16, 2008, now U.S. Pat. No. 8,876,816, issued Nov. 4, 2014, which claims priority to United Kingdom Application No. 0709993.0, filed May 24, 2007, and claims the benefit of Provisional Application No. 60/929,111, filed Jun. 13, 2007, the entire contents of each of which are hereby incorporated herein by reference.

FIELD OF THE INVENTION

This invention relates to an electrosurgical system having a radio frequency (RF) generator for generating RF power and an electrosurgical instrument, typically in the form of a handpiece that is detachable from the generator. The invention also relates to an electrode assembly which forms part of or constitutes an electrosurgical instrument that is connectible to an electrosurgical RF generator.

BACKGROUND OF THE INVENTION

Such an electrosurgical system is known from U.S. Pat. No. 6,074,386 (Goble et al). In this system, the generator forms part of a first unit and the electrode assembly forms part of a second unit, the second unit being detachably connectible to the first unit such that RF power can be conveyed to the electrode assembly. The second unit includes a capacitor the capacitance value of which is indicative of a characteristic of the electrode assembly. The generator includes a sensing circuit having an inductance which, when the first unit is connected to the second unit, forms a resonant circuit the resonant frequency of which depends on the capacitance value. By arranging for this resonant circuit to form part of an oscillator, it is possible to generate an alternating signal the frequency of which is indicative of the above-mentioned characteristic of the electrode assembly and, furthermore, the oscillator output signal is fed to a controller configured to adjust the output of the generator in response to the oscillator signal so as to suit the indicated electrode assembly characteristic. It follows that different electrode assemblies having different characteristics can be provided with capacitors of different capacitance values so that, when an electrode assembly is attached to the generator, the generator is automatically adjusted to deliver the right output for that electrode assembly.

SUMMARY OF THE INVENTION

It is an object of the invention to provide a more versatile identification and auxiliary data information system.

According to a first aspect of the invention, an electrosurgical system comprises a first unit including a generator for generating radio frequency (RF) power, and a second unit including at least part of an electrosurgical instrument associated with the generator, the second unit being detachably electrically connectible to the first unit such that RF power can be conveyed to the second unit; wherein the second unit includes a passive electrical identification component having a parameter of a finite non-zero value identifying the second unit; and wherein the first unit comprises a sensing circuit including a second electrical component, a signal source arranged to provide a voltage step-change, and a signal detector, the second electrical component forming a combination circuit with the identification component when the second unit is connected to the first unit, the signal source and signal detector being arranged such that provision of a voltage step-change by the signal source causes a transient response of the combination circuit dependent on the parameter value and the detector detects a characteristic of the transient response to generate a detector output signal representative of the parameter value, wherein the first unit further comprises a controller connected to the sensing circuit to receive the detector output signal. The controller is configured to identify the unit in response to the detector output signal and/or to adjust the output of the generator in response to the detector output signal so as to suit the second unit. Preferably, the passive electrical identification component is a capacitance and the second electrical component is an inductance which forms a resonant circuit with the identification component when the second unit is connected to the first unit, the signal source and signal detector being arranged such that the voltage step-change causes ringing of the resonant circuit at a frequency dependent on the parameter value and the detector detects a characteristic of the ringing to generator the detector output signal.

The transient nature of the response detected by the detector allows other signals to be passed between the first and second units. For instance, the second unit may include a digital device having a memory containing information which can also be used to adjust the generator, or which can be used to provide information to the user. Typically the digital device stores information relating to the extent of use of the electrosurgical instrument, this information being updated as the instrument is used so that, for example, operation of the generator can be inhibited once a predetermined usage limit has been reached. An interchange of signals may take place between the digital device and a controller within the generator for updating software instructions contained in the controller to configure the generator for newly introduced electrosurgical instruments or to adjust recommended operating parameters associated with an existing range of instruments.

The signal detector may be arranged to detect the frequency of the ringing, or the interval between first and second instants at which a ringing waveform produced by the resonant circuit crosses a predetermined reference level. Typically the detector includes a comparator for converting the ringing into a binary signal and a counter coupled to the comparator and arranged to count pulses of the binary signal. The detector may include a pulse width measuring device coupled to the comparator to produce a signal representative of the width of at least one pulse of the binary signal. In both cases, the detector output signal is indicative of the capacitance value of the capacitor in the second unit and can be used to adjust the generator.

In an alternative embodiment, the second electrical component is a resistance which forms a resistance-capacitance (RC) combination when the second unit is coupled to the first unit, the combination having an RC time constant dependent on the value of the capacitance. In such a case, the signal source and the signal detector may be arranged such that the voltage step-change causes a monotonically time-varying voltage to be generated by the resistance-capacitance combination and the detector is adapted to generate a detector output signal representative of, for instance, the rate of change of the time-varying voltage.

In the preferred embodiment, the first unit and the second unit have respective interengaging pairs of RF power conduction contacts for conveying RF power from the generator to the instrument, wherein one contact of each such pair forms part of a signal path between (i) the signal source used to produce the transient response for identifying the instrument to the generator and (ii) the electrical identification component in the instrument when the instrument is connected to the generator. Thus, the RF power conduction path and the above-mentioned combination circuit or resonant circuit have a common contact on each of the first unit and the second unit.

In a particularly advantageous arrangement, the first and second units have, respectively, a first set of contacts and a second set of contacts arranged so as to interengage when the second unit is connected to the first unit, the first set of contacts including one pair of contacts which are interconnected by the identification capacitor and which are also connected to the digital device so as to serve either for supplying power from the generator to the digital device or for conveying data from the digital device to the generator and, if appropriate, vice versa. The signal source in the first unit is typically operable to apply a DC potential between a pair of contacts in the first set which engage the said pair of contacts in the second unit so as to power the digital device, the signal source and the signal detector being further operable respectively to generate an interrogation pulse during which the supply of power from the first unit to the second unit for the digital device is interrupted. The interrogation pulse is preferably a square pulse, but may take other forms, e.g. an impulse or spike. The interrogation pulse may include at least a first edge constituting the said voltage step-change causing the transient response, the transient response characteristic being detected whilst the supply to the second device is interrupted. Data from the digital device may be conveyed to the generator only after the interrogation pulse. This may be achieved by configuring and connecting the digital device so as to detect the end of the interrogation pulse and enabling data output from the digital device to the generator (and in the reverse direction, if required) in response to such detection.

The second unit may have two or more passive electrical identification components, e.g. two or more capacitors, each connected between a respective pair of the second set of contacts. In this case, the configuration and connection of the digital device to these pairs of contacts may be such that the digital device is powered via one pair and outputs data via another pair. Alternatively, the digital device may both draw power and output data via a common pair of contacts within the second set.

According to another aspect of the invention, an electrode assembly for an electrosurgical system comprises at least one tissue treatment electrode; a mounting portion for detachably securing the assembly to another part of the system; a passive electrical identification component arranged to form a combination circuit with a second electrical component in a sensing circuit associated with the said other part of the system, the identification component having a parameter of a finite non-zero value indicative of the electrode assembly; a digital device including a memory; and a set of contacts for engaging contacts on the said other part of the system; wherein the set of contacts includes a pair of contacts which are interconnected by the identification component and which are also connected to the digital device so as to serve for at least one of (a) supplying power from the said other part of the system to a power supply terminal of the digital device and (b) conveying data from a data output of the digital device to the said other part. The electrode assembly is typically a monopolar, bipolar or tripolar assembly, the figures and the following description show the use of the invention with a bipolar assembly having two electrodes, one of which is coupled to one of the contacts of the pair interconnected by the identification component so that that contact serves a dual purpose of being both part of the RF power delivery circuit and an identification circuit including the identification component.

Variants of the invention may include a system in which RF power delivery and completion of an identification circuit are carried out via a common pair of contacts. The digital device may be self-clocked using an embedded clock, e.g. using Manchester non-return to zero encoding.

In the preferred embodiment the second unit comprises an electrosurgical instrument in the form of a handpiece and a connector including the above-mentioned second set of contacts, the connector and handpiece being interconnected by a multiple core cable, and the identification capacitor or capacitors are located in the connector body. Where a digital device is included, this may be housed in the connector body as well. The connection interface between the first unit and the second unit is between the electrosurgical unit and an electrosurgical generator, the generator including one or more comparators for processing the transient response resulting from application of a voltage step-change to each combination circuit or resonant circuit.

It is possible, however, for the connection interface to be between an electrode assembly which is detachable from a handpiece body, the capacitor or capacitors and/or digital device being housed within the electrode assembly.

When the terms "digital device" and "memory" are used herein, it is to be understood that although a digital memory device is the preferred component, due to its sophistication, other output circuits capable of generating an identifiable characteristic signal could be employed. As an example, a circuit (normally digital, but alternatively analogue circuits are conceivable) could be provided which generates a characteristic output, either continuously or in response to some form of prompt. These circuits could be used to convey the data to the said other part of the system as previously described.

Accordingly, the invention extends to an electrosurgical system comprising a first unit including a generator for generating radio frequency power, and a second unit including an electrode assembly, the second unit being detachably connectible to the first unit such that radio frequency power can be conveyed to the electrode assembly, wherein the second unit firstly includes a passive electrical identification component having a parameter of a finite non-zero value indicative of a characteristic of the electrode assembly, and the second unit additionally includes an output circuit adapted to generate an identifiable characteristic signal, the first unit firstly including a sensing circuit for determining the value of the electrical identification component so as to identify the second unit when the second unit is connected to the first unit, and the first unit additionally including means for receiving the identifiable characteristic signal from the output circuit when the second unit is connected to the first unit.

Where the output circuit comprises a digital memory device containing digital information, the means for receiving the identifiable characteristic signal conveniently comprises a look-up table into which the digital information is transferred. As described in previously referred to U.S. Pat. No. 6,074,386 (Goble et al), the entire contents of which are incorporated herein by reference, the first unit conveniently includes a second passive electrical component and an oscillator, the oscillator and a parameter of the identification component forming a resonant circuit when the second unit is connected to the first unit and the oscillator is oscillating at the resonant circuit's resonant frequency, the sensing circuit generating an output signal based on the oscillator's oscillating frequency and being representative of the parameter value, the first unit further including a controller connected to the sensing circuit and receiving the output signal, the controller being configured to adjust the output of the generator in response to the output signal from the sensing circuit so as to suit the characteristics of the identified electrode assembly.

The first unit conveniently comprises the generator, a connector, and a cable for coupling the generator to the connector, the cable including conductors for coupling the identification component to the sensing circuit, and wherein the second unit is in the form of an electrode assembly including a connector which mates with said connector of the first unit.

The sensing circuit is conveniently configured to detect a plurality of different values of said parameter, and the controller is configured to set the output power of the generator according to the output signal provided by the sensing circuit and representative of the identification component parameter. Where digital information is transferred to the look-up table, this includes the parameters for the output of the generator so as to suit the characteristics of the identified electrode assembly. The digital information transferred to the look-up table conveniently includes one or more of the output power, maximum current or voltage settings for the generator when used with the identified electrode assembly. The digital information transferred to the look-up table conceivably includes the parameters for the output of the generator so as to suit the characteristics of electrode assemblies other than the identified electrode assembly.

BRIEF DESCRIPTION OF THE DRAWINGS

The invention will now be described by way of example with reference to the drawings in which.

DETAILED DESCRIPTION OF THE INVENTION

Figure 1:
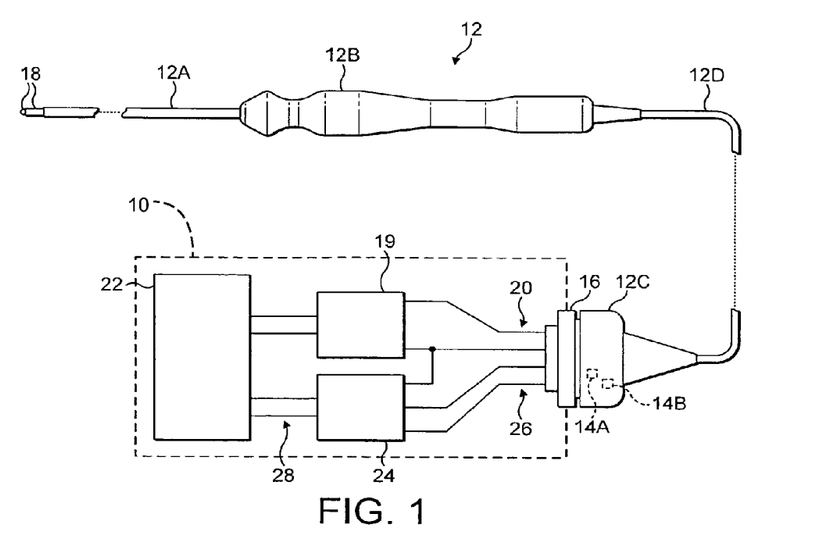
FIG. 1 is a diagrammatic representation of an electrosurgical system in accordance with the invention.

Referring to FIG. 1, an electrosurgical system in accordance with the invention comprises a first unit in the form of an electrosurgical generator for generating radio frequency power, and a second unit comprising an electrosurgical instrument in the form of a pencil-grip handpiece 12 including an electrode assembly, a handpiece body 12B, and a connector 12C which is coupled to the handpiece body and the electrode assembly by a cable 12D. Housed within the connector 12C are two passive electrical identification components 14A, 14B which, in this case, are capacitors. The connector 12C is a multiple contact plug which mates with a multiple contact socket 16 on the generator 10 so that the instrument 12 can be removably connected to the generator.

In this embodiment of the invention, the electrode assembly 12A is a bipolar assembly having two tissue treatment electrodes 18. However, the assembly may comprise single or multiple electrode elements, in other words, monopolar, tripolar or multiple electrode assemblies. In the illustrated embodiment, the electrodes 18 are connected via respective electrical conductors running through the handpiece body 12B and the cable 12D to a respective pair of contacts (not shown in FIG. 1) in the plug 12C. The capacitors 14A and 14B are also connected to a respective pair of contacts (not shown in FIG. 1) in the plug 12C.

The generator comprises a radio frequency (RF) oscillator 19 with a pair of RF output lines 20 for feeding RF energy via the socket 16 to the RF power contacts in the instrument plug 12C for energising the bipolar electrodes 18. The RF oscillator 19 is controlled by a controller 22 which has connections to a user interface (not shown). Coupled to the controller is an electrode identification circuit having connections 26 to the socket 16 for connecting to the capacitors 14A, 14B. When the instrument 12 is coupled to the generator 10, the electrode identification circuit 24 can be used to measure the value of the capacitors, detector output signals being conveyed by lines 28 to the controller 22 for controlling the RF oscillator 19 in response to the value of the capacitors 14A, 14B. It will be appreciated that, by providing capacitors 14 of different values in different instruments 12, the value of the capacitors can be used to identify the instrument 12 and thereby cause adjustment of the generator RF output to suit each respective instrument when it is connected. To this extent, the system operates largely as described in U.S. Pat. No. 6,074,386, the entire disclosure of which is incorporated in the present specification by reference.

Measurement of capacitor values in the system in accordance with the invention will now be described with reference to the simplified circuit diagram of FIG. 2 and the accompanying waveform diagrams of FIG. 3.

Figure 2:
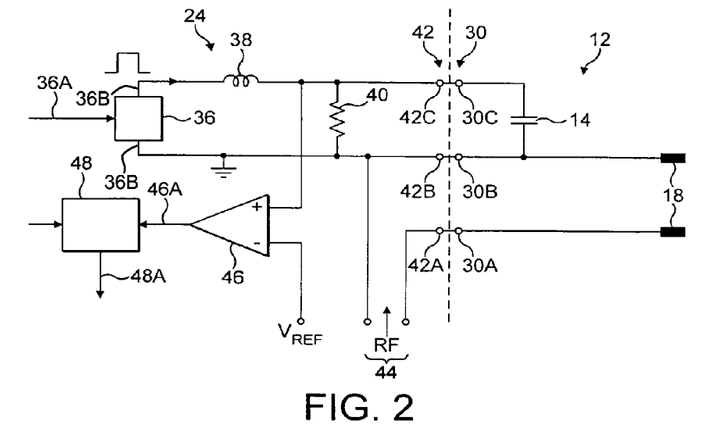
FIG. 2 is a circuit diagram of an electrosurgical instrument and identification circuitry for allowing an electrosurgical generator to be adjusted in response to connection of an electrosurgical instrument including a passive electrical identification component.

Referring to FIG. 2, the electrosurgical instrument 12 (in the form of an electrode assembly having two electrodes 18) has a set of contacts 30, two of which constitute a pair of RF power contacts (30A, 30B) which are coupled to the electrodes 18 of the instrument. An identification capacitor 14 is connected between one of the RF power contacts 30B and a third, identification contact 30C of the set so that the electrodes 18 and the capacitor 14 have one common contact 30B. On the generator side, the electrode identification circuit comprises a signal source 36 having a timing input 36A connected to the controller. The source 36 is configured to generate an interrogation pulse across a pair of source output lines 36B. Connected in series between the source 36 and the capacitor 14 is an electrical component in the form of an inductance 38. Downstream of the inductor 38 is a shunt-connected damping resistance 40.

The generator has a set of contacts 42 which mate with the contacts 30 of the instrument 12, as shown. Output lines 44 from the RF oscillator 19 (not shown in FIG. 2) are coupled to contacts 42A, 42B which mate with contacts 30A, 30B of the instrument 12 so that electrosurgical RF energy is conveyed to the electrodes 18 when the instrument 12 is connected to the generator. A third contact 42C on the generator is connected via the inductor 38 to one of the output lines 36B of the signal source 36, whilst the contact 42B which mates with instrument contact 30B acting as a common contact for the capacitor 14 and one of the electrodes 18 is not only connected to the output lines of the RF oscillator, but also to the other output line 36B of the signal source 36.

It will be appreciated that when the instrument 12 is connected to the generator, the capacitor 14 in the instrument and the series inductance 38 in the identification circuit 24 together form a series-resonant combination circuit having a resonant frequency determined by the values of the capacitor 14 and the inductor 38. Since capacitor 14 has different values depending uniquely on the instrument 12 in which it is contained, the resonant frequency identifies the instrument 12.

Coupled to the connection between the inductor 38 and the capacitor 14 is one input of a comparator 46 the other input of which is connected to a reference voltage source $V_{REF}$. This reference voltage is at a predetermined potential with respect to the other arm of the resonant circuit formed by capacitor 14 and inductor 38 (here the output line 36B of the signal source which is not connected to the inductor 38). Comparator 46 has an output 46A connected to a signal processing circuit 48 which, in turn, feeds the controller 22 (see FIG. 1) via its output 48A.

It will be appreciated that when the voltage step-change represented by the leading edge of the interrogation pulse generated by signal source 36 is applied to the resonant combination of capacitor 14 and inductor 38, a ringing signal is generated at the junction between capacitor 14 and inductor 38, the ringing occurring at the resonant frequency referred to above. Owing to the presence of the parallel resistance 40, the ringing signal decays predictably. In practice, the value of the resistance 40 is chosen such that its effect upon the decay rate of the ringing of the signal is minimised, but its effect in the presence of noise is maximised, its main purpose is for EMC protection and to keep the ringing of the resonant network to predictable values. The value of the voltage reference source $V_{REF}$ is selected such that, during the interrogation pulse, the ringing signal crosses over the reference voltage several times, with the effect that a corresponding binary signal appears at the output 46A of the comparator 46, the binary signal taking the form of a squarewave having a repetition rate equal to the resonant frequency of the capacitor/inductor combination. In this example, the signal processing circuit 48 measures the interval between successive edges of the squarewave, thereby detecting the pulse width of the squarewave signal and, hence, the period of the ringing signal. As an alternative, signal processing circuit 48 may employ a counter arranged to count the number of changes of state of the output signal from the comparator 46 as a means of determining the ringing frequency or period.

Figure 3:
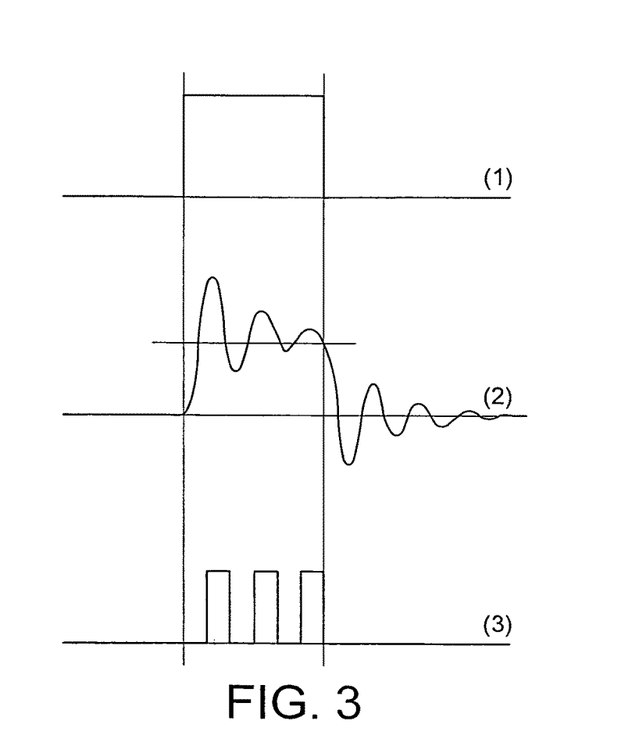
FIG. 3 is a set of three waveform diagrams relating to the circuitry of FIG. 2.

The interrogation pulse is shown by waveform diagram (1) in FIG. 3. The ringing signal is shown in diagram (2) and the squarewave signal outputted by the comparator 46 is shown by diagram (3) in FIG. 3.

It will be appreciated that detecting the transient response of the resonant combination of the capacitor 14 and inductor 38 rather than using the resonant combination to determine the frequency of oscillation of an identification circuit oscillator as in U.S. Pat. No. 6,074,386, allows the contacts coupling the identification capacitor 14 to the identification circuit of the generator 10 to be used for different purposes at times other than during the transient response. In other words, sensing oscillations in the resonant combination only for a short period permits sharing of the connections, in ways that will be described below.

In the system described above with reference to FIG. 2, the identification components (capacitors 14A, 14B) are housed a connector 12C forming part of an instrument 12 detachably connected to the generator 10. In this case, the generator 10 constitutes the "first unit" and the complete instrument 12 constitutes the "second unit", the connection interface occurring between the plug 12C and the socket 16. In an alternative embodiment, the first unit may be an instrument body and the second unit a sterilisable instrument part (not shown). Thus, the instrument 12 may have a detachable electrode assembly 12A and the capacitor may be housed in the detachable part, so that the connection interface, for the purpose of identification, is not between the plug 12C and the socket 16 but between mutually separable parts of the instrument 12.

Figure 4:
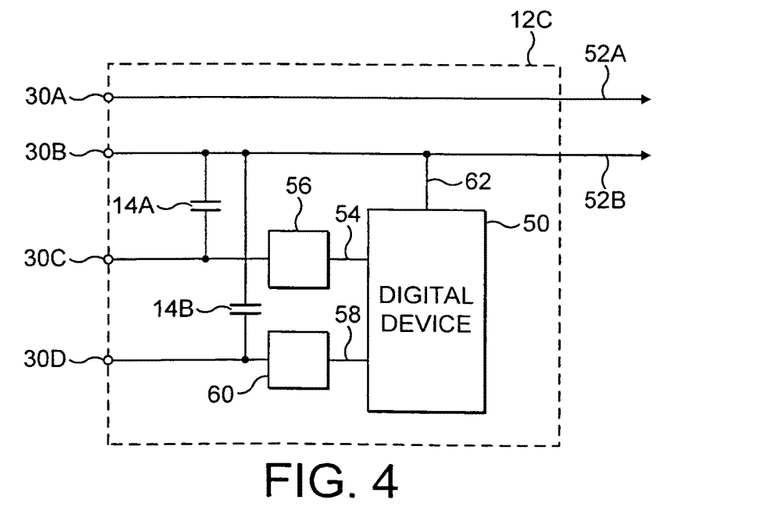
FIG. 4 is a circuit diagram of a connector forming part of an electrosurgical instrument which itself forms part of the electrosurgical system of FIG. 1.

Referring to FIG. 4, in a preferred embodiment of the invention, the connector 12C houses two identification components 14A, 14B (e.g. two capacitors of different value. The case of the two values of capacitance being equal is used as an error or fault condition indicator, which may be as a result of a short circuit in the plug, etc. The connector 12C also houses a digital device 50 which operates through the same contacts of the connector 12C as the capacitors 14A, 14B. In this case, the connector 12C has a contact set 30 comprising four contacts two of which 30A, 30B are used for RF power and are coupled to lines 52A, 52B passing through the connector to the cable 12D and electrodes 18 (see FIG. 1). In this case, both capacitors 14A, 14B have one terminal connected to one of the RF power contacts 30B. The other terminals are connected to respective identification contacts 30C, 30D. However, these identification contacts 30C, 30D are also used for functions associated with the digital device 50. As will be seen from FIG. 4, digital device 50 has a power supply line 54 coupled to identification contact 30C via an intermediate circuit 56, and a data output 58 coupled to identification contact 30D via a second intermediate circuit 60. A local 0V signal and power return terminal 62 of the digital device 50 is coupled to the line 52B, thereby sharing contact 30B not only with the electrodes of the instrument, but also with the first capacitor 14A.

Figure 5:
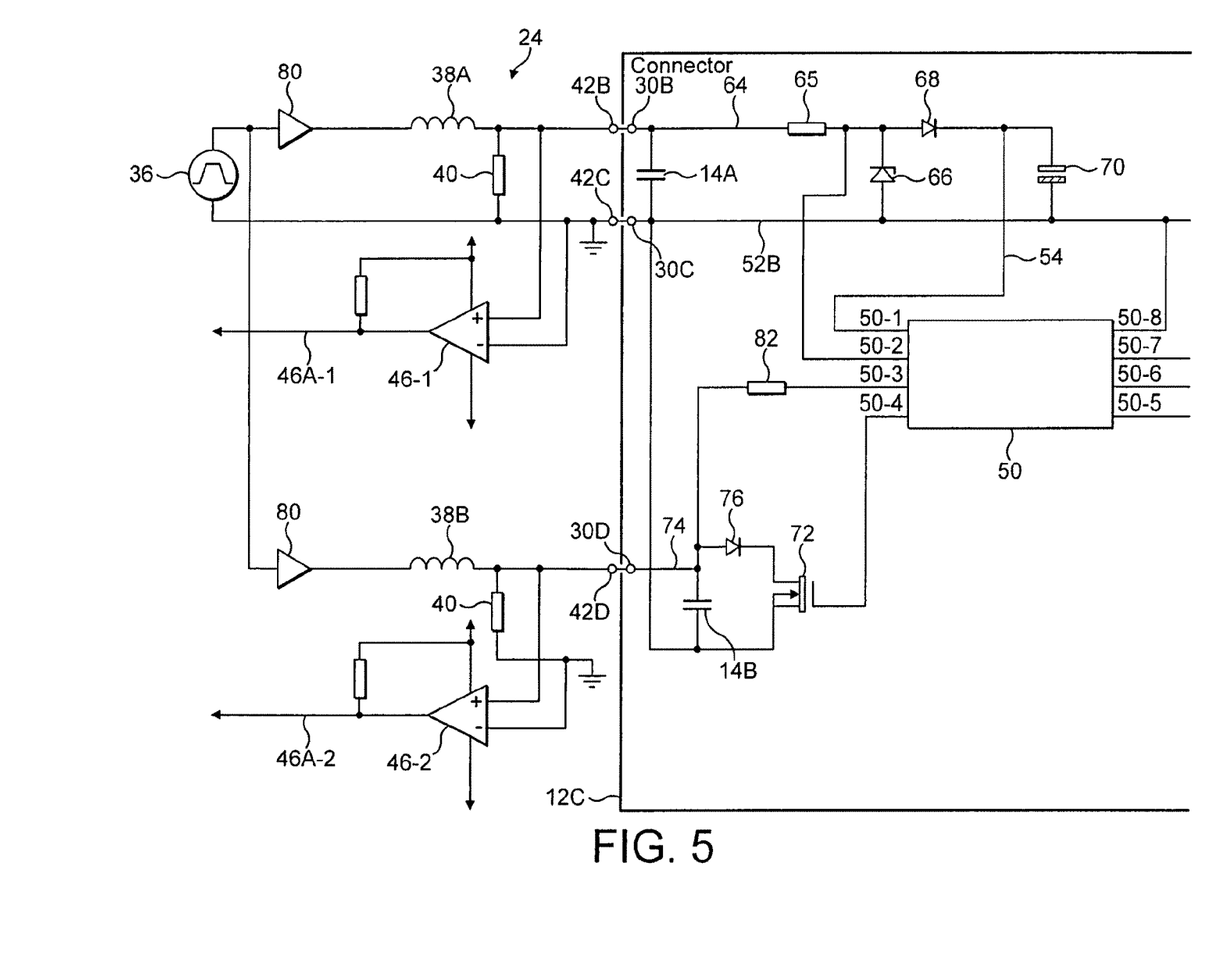
FIG. 5 is a detailed circuit diagram of the connector shown in FIGS. 1 and 4, together with part of an electrosurgical generator of the system of FIG. 1.

The circuitry of the connector 12C is shown in more detail in FIG. 5 together with the identification circuitry forming part of the generator.

Referring to FIG. 5, as shown in FIG. 4, the identification components, capacitors 14A, 14B have a common line 52B in the connector 12C which they share with the RF power transmission circuit. This line is the 0V reference for this part of the generator. In practice, isolation barriers are implemented for compliance to international standards, this has the effect that parts of the generator have local 0V reference points. In this embodiment, the digital device 50 is a CMOS microcontroller PIC12F683 available from Microchip Technology, Inc. Alternative digital devices include an EEROM, a CPLD (complex programmable logic device) or a gate array. The PIC12F683 has 256 bytes of EEROM that can be read from and written to, it also has program FLASH memory that could contain values that are transferred to the generator. It also has three pins that can be used for daisy-chaining additional devices (I2C EEROMS, PICs, or 1-wire "iButton" devices). Apart from the supply pins 50-1, 50-8, the pins of this digital device can be programmed to perform different functions. For instance, pin 50-2 can be configured to receive an external clock signal or to receive a pulse enabling an internal clock. It is the latter function that is assigned to the pin in the present example. Pin 50-3 is configured as an input to receive data from the generator and pin 50-4 is configured as a data output to send data to the generator. In accordance with preferred features of the invention, the digital device 50 is powered through contacts which are also used for instrument identification, in this case the pins which are interconnected by the first identification capacitor 14A. Data is outputted via the contact (30D) used for connecting the second identification capacitor 14B to the identification circuitry in the generator. Intermediate components are included between the digital device and both capacitors. In particular, the digital device 50 is powered from an ID line 64 via a voltage regulating and rectifier stage comprising series resistance 65, a shunt zener diode 66 and a series rectifying diode 68. The supply line 54 is smoothed by a shunt capacitor 70. Data from data output 50-4 is fed to a semiconductor device used as a switch 72, in this case a FET device, but it could be a NPN-type transistor. This semiconductor switch is coupled across the second ID capacitor 14B so that it effectively shorts the second ID line 74 to ground when the data output 50-4 is logic high. A diode 76 isolates the capacitor 14B from the digital device when switch 72 is off and stops negative voltages generated by the resonant network being place across the switch 72. it also stops the FET 72 switch damping the series resonant network. The second ID line is additionally connected via a series resistance to pin 50-3 of the digital device 50. The buffers 80 have limited ability to supply current and can thus withstand the action of the switch 72 shorting them out without damage.

The identification circuitry 24 in the generator has two transient signal sensing circuits each arranged largely as described above with reference to FIG. 2. Additional features include the setting of the reference voltage for the comparators 46A, 46B as the ground potential, and the use of a common signal source 36 for both sensing circuits. This signal source is coupled to the inductors 38A, 38B by respective buffers 80 and normally powers the ID lines 64, 74 high with respect to ground so that the digital device 50 can be powered via the regulating circuitry 64-70 described above and to maintain a voltage across the data output switch 72.

Interrogation pulses generated by the signal source 36 are negative pulses. The voltage step-change constituting the leading edge of an interrogation pulse causes ringing of the two resonant circuits formed by capacitor 14A and inductor 38A and capacitor 14B and inductor 38B respectively. As described above, the comparators 46-1 and 46-2 convert the ringing signal in each case to respective binary signals which are outputted on lines 46A-1 and 46A-2 for further processing. Such processing, in this example, comprises timing the respective time intervals between zero-crossings of the ringing waveform in each case to determine the period of the ringing signal and, hence, the value of the capacitor 14A, 14B. Preferably, this measuring function is performed by elements (not shown) in the generator which also include the signal source 36. These measuring elements may be discrete logic devices, e.g. those from the 74 series, or firmware, e.g. in a CPLD or software in a microprocessor. Ringing of the two resonant circuits occurs during the interrogation pulse, i.e. whilst the outputs of buffers 80 are low. The trailing edge at the end of the interrogation pulse is detected by the digital device on its clock enable input 50-2 and power to the digital device 50 (supplied via pins 50-1 and 50-8) is resumed, the supply voltage on supply line 54 having been maintained during the interruption caused by the interrogation pulse by the smoothing capacitor 70.

In this embodiment, the values of the identification capacitors 14A, 14B are different and each have a selected value within the range of from 200 pF to 220 nF depending on the electrosurgical instrument of which they form part. The inductors 38A, 38B are each 30 mH. This yields a potential resonant frequency range of from 2 kHz to 63 kHz. The length of the interrogation pulse is 1 ms, i.e. twice the period of the lowest frequency ringing signal (corresponding to the highest capacitor value in the above range). In variants of this circuit, the interrogation pulse width may be as low as one half of the period of the lowest frequency ringing signal.

Figure 6:
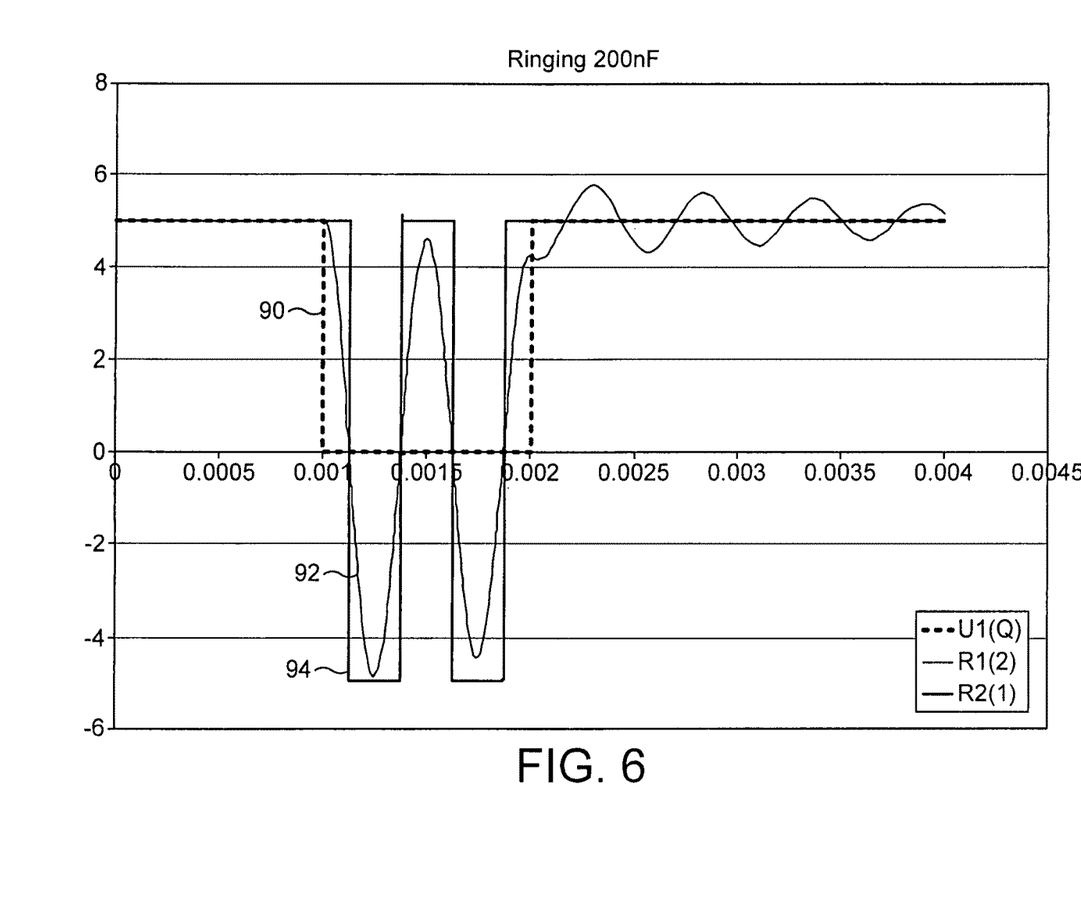
FIG. 6 is a waveform diagram showing behaviour of the circuitry shown in FIG. 5 when the identification component has a first preselected parameter value.
Figure 7:
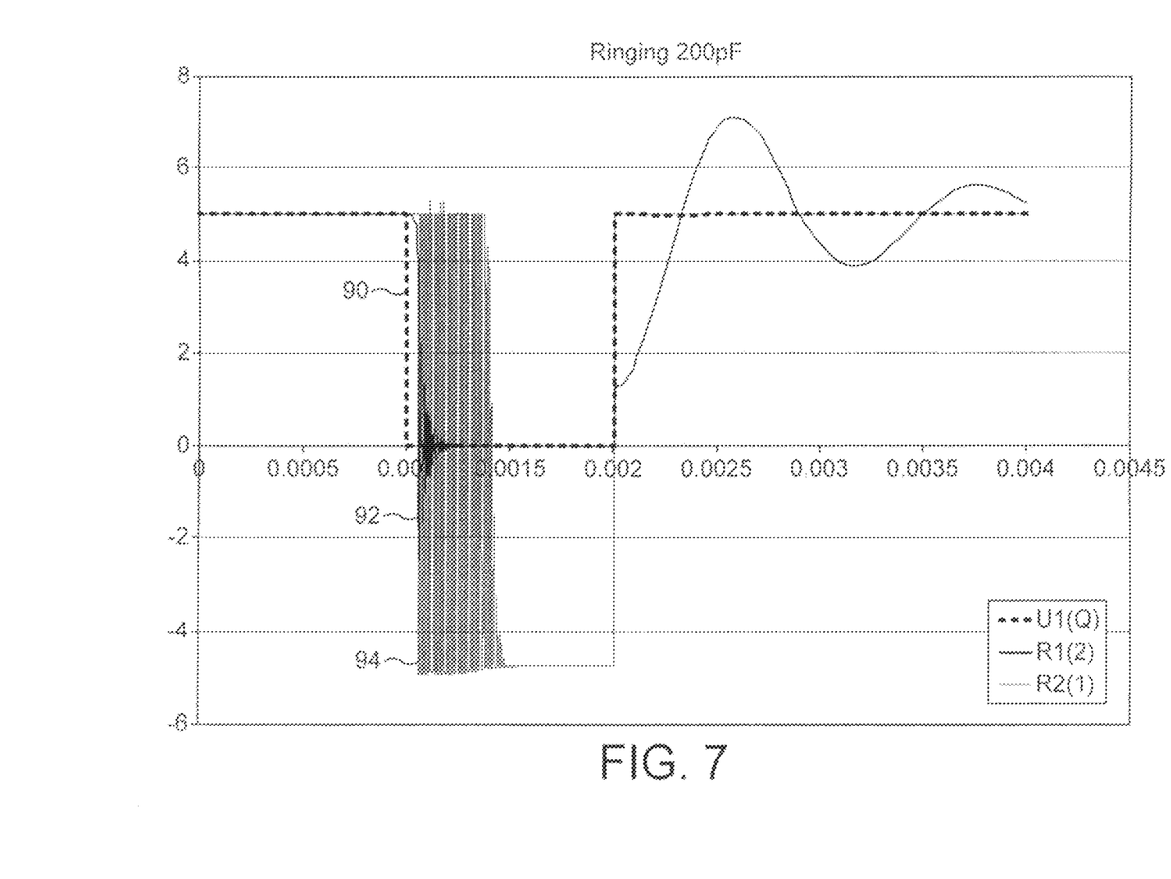
FIG. 7 is a waveform diagram showing behaviour of the circuitry of FIG. 5 when the identification component has a second, smaller, preselected parameter value.

Operation of the sensing circuits is illustrated in FIGS. 6 and 7. Referring to FIG. 6, the interrogation pulse is seen as a negative-going squarewave pulse 90. Upon commencement of the pulse, the negative-going voltage step-change applied to the inductor 38A, 38B causes the ID line on the junction of the inductor 38A, 38B and the capacitor 14A, 14B to fall in voltage from an initial +5V as shown by trace 92, thereafter ringing as described above. A third trace shown in FIG. 6 indicates the voltage at the output of the respective comparator 46-1, 46-2 which is a squarewave 94 changing state at each zero-crossing of the ringing signal 92. The waveforms illustrated in FIG. 6 are those produced when the relevant identification capacitor has a value of 200 nF. As will be seen, this yields four zero-crossings during the interrogation pulse, one or more of the intervals between successive zero-crossings being measured by the processing circuitry downstream of the respective comparator. At the end of the interrogation pulse 90, the buffer output 80 executes a positive-going step change from 0V to +5V, with the result that the identification line once again settles at about +5V, albeit with some ringing, as shown.

If the capacitor 14A, 14B has a lower value, there are more ringing cycles during the identification pulse, notwithstanding the decay produced by the shunt resistance 40. Multiple oscillations produced by a capacitor value of 200 pF are illustrated in FIG. 7. The decaying ringing signal and the corresponding comparator output are again shown by reference numerals 92 and 94 respectively.

Referring again to FIG. 5, detection of the rising edge at the end of the interrogation pulse on input 50-2 of the digital device 50 has the effect of switching on FET data output switch 72, thereby signalling detection of the rising edge to the generator circuits (coupled to the output line 46A-2 of the second comparator 46-2). In practice, the signal source 36 outputs the negative-going interrogation pulse, and the ringing signal pulse width is counted to determine the value of the first identification capacitor 14A. If no response is detected on the output line 46A-2 of the second comparator 46-2, the generator microprocessor assumes that the instrument connected to it has no digital device 50, merely identification capacitors 14A, 14B, whereupon it outputs a second negative-going pulse to identify the second ID capacitor. If, on the other hand, there is a response, the microprocessor outputs a further interrogation pulse or pulses in order to measure the ringing signal produced by the second resonant circuit 14B, 38B, or it can monitor the comparator output line 46A-2 for signals from the digital device 50 fed via data output 50-4. The second ID line 74 is preferably bi-directional. The microprocessor in the generator can use the signal source 36 to send information to the digital device 50, e.g. an information address. This may be synchronised with pulses on the first ID line 64 (used as a clock line) or, as in the present embodiment, or may be asynchronous (i.e. clock-encoded, e.g. using Manchester encoding). The first ID line 64 can, after the first pulse used for identification using the capacitor 14A, be used for data direction control of the second ID line 74. In this latter case it can be regarded as a read not write line. Once it has been established that a digital device is present in the connector 12C, data can be placed on the second I.D. line by the microprocessor. The first I.D. line is then used as a write strobe, the digital device takes the data from the second I.D. line and transfers it to its internal EEROM or presents it on the cascade pins 50-5 to 50-7 for storing in an external memory device. Alternatively, once communication has been established and a self-clocking protocol is used, space (defined in the time domain) within data packets can be reserved for data transfer from the generator to the digital device.

It can be noted that pin 50-3 is an input that can be used by the digital device to verify the action of the FET switch 72. There is a series resistor 82 which limits the current into the pin data input 50-3 when the resonant network generates voltages higher than the power supply level of the digital device.

Summarising, the arrangement described above with reference to FIG. 5 allows the generator characteristics to be adapted for improved electrosurgical performance using identification capacitors forming part of the detachable electrosurgical instrument, the capacitors having unique values characteristic of the instrument, whilst at the same time allowing the transfer of information from a digital device housed in the instrument to enhance further the operation of the electrosurgical generator. The digital device 50 includes memory in which may be stored information written in by the manufacturer of the instrument or during use of the instrument. The information may include parameters that are used for generator control and which are transferred from the instrument before a surgical procedure is started. The information may include dates, such as date of manufacture and software-upgrading information for upgrading software in the generator. In addition, the information may include values obtained during a surgical procedure and which are transferred from the generator to the instrument. Information stored within the instrument may be examined by any generator to which it is connected. For example, the information recorded during a previous procedure may be examined by the generator some time after the procedure. Such information may include the dates and elapsed time of the procedure so as to preclude multiple use of a single use instrument, for instance.

Figure 8:
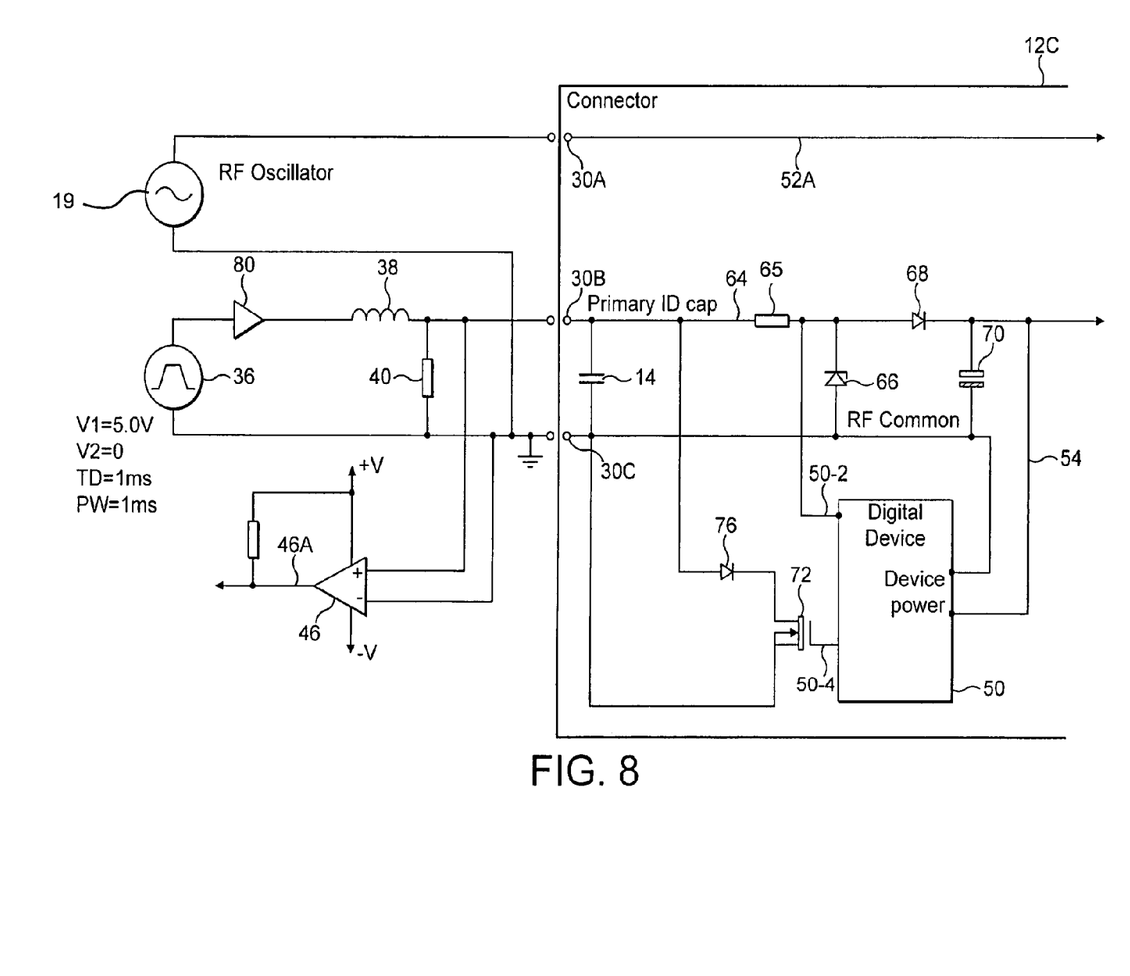
FIG. 8 is a circuit diagram of part of an alternative electrosurgical system in accordance with the invention.

Referring to FIG. 8, in an alternative system in accordance with the invention, powering of the digital device and the transmission of data from the device are both performed via a common ID line 64 and contact 30. The power supplied to the connector for the digital device is interrupted, in this case, not only by the interrogation pulse but also by data outputted from the digital device 50 causing the FET switch 72 to short the ID line 63 to ground. The encoding scheme relies on an embedded clock using, e.g. Manchester encoding (non-return to zero). It will be noted that, in this embodiment, only three connector pins are needed for (i) conducting RF power to the instrument, (ii) for identification, and for (iii) data exchange with the digital device 50.

Figure 9:
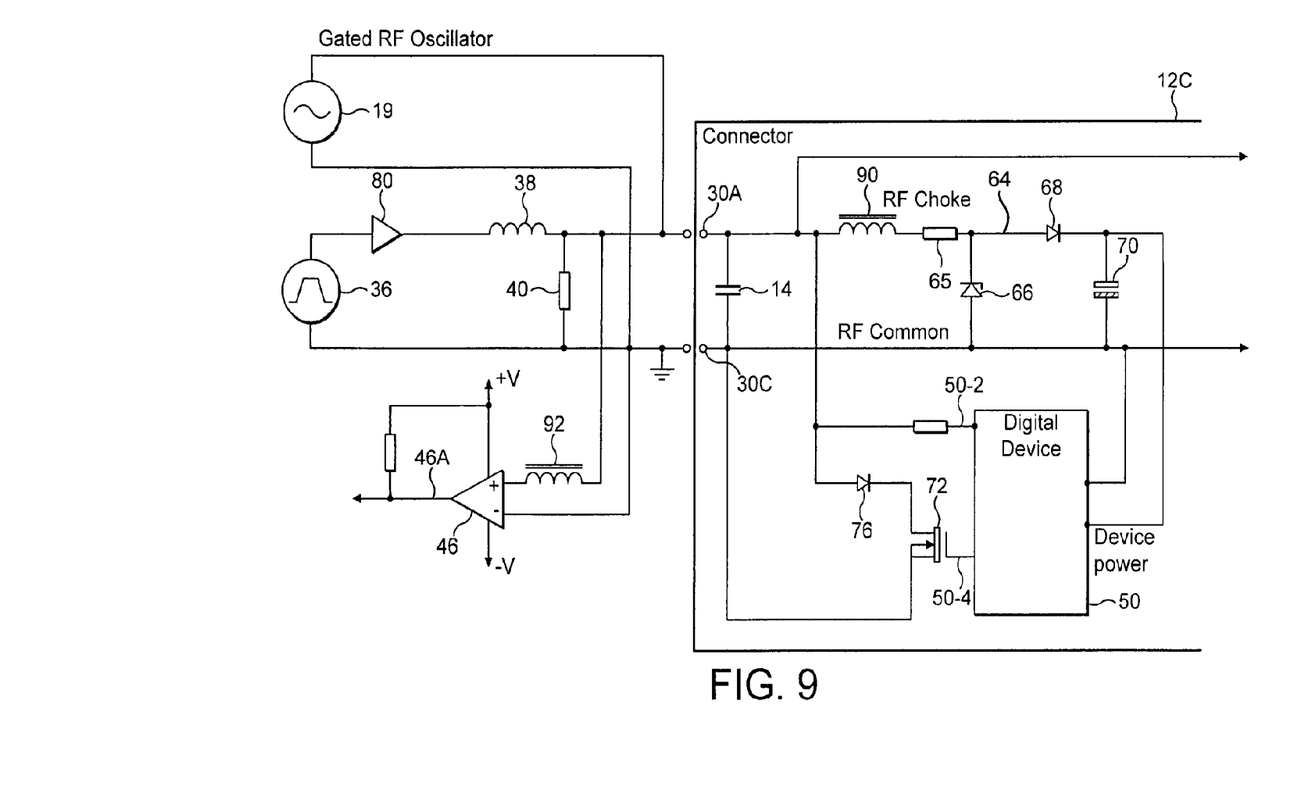
FIG. 9 is a circuit diagram of part of a further alternative electrosurgical system in accordance with the invention.

In a variation of the system described above with reference to FIG. 8, the identification and data transfer functions share a single pair of connector contacts with the RF power lines, as shown in FIG. 9. In this case, the RF oscillator 19 is connected directly to the same line 64 used for identification and data transfer and the same contact 30A. An RF choke 90 is connected in series in the instrument between the ID line 64 and the intermediate supply components 65-70 for the digital device 50. A second RF choke 92 in the generator is connected in series between the ID line 64 and the signal input of the comparator 46. These chokes protect the identification components against high radio frequency voltages produced by the RF oscillator 18. The RF oscillator 18 is gated by the controller (FIG. 1) so as to be energised only when identification signals are not present, and vice versa.

Figure 10:
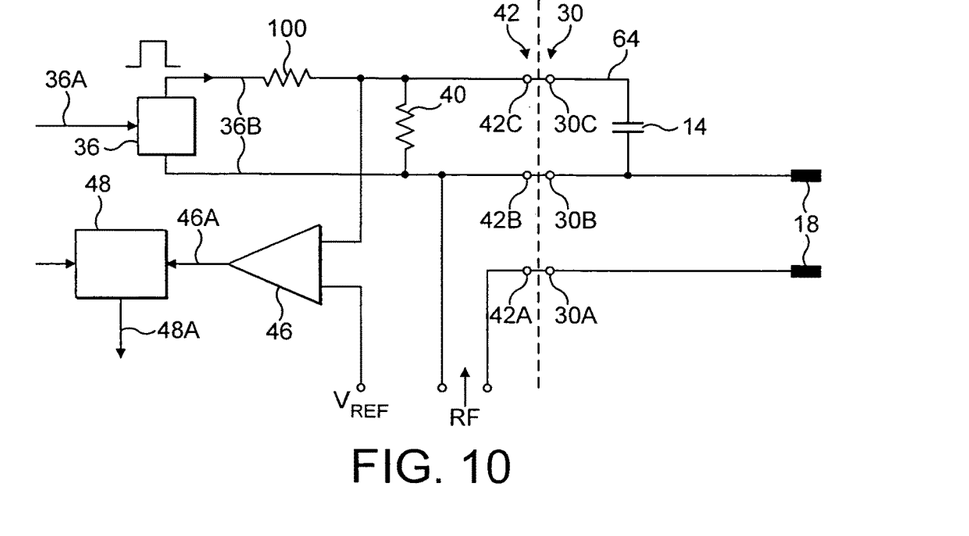
FIG. 10 is a simplified circuit diagram of part of a fourth electrosurgical system in accordance with the invention.
Figure 11:
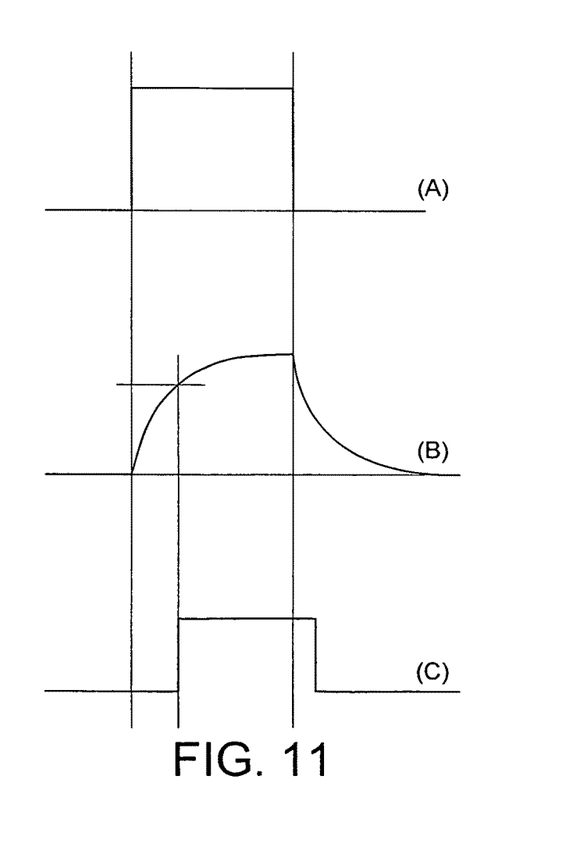
FIG. 11 is a set of waveform diagrams illustrating the behaviour of the simplified circuit of FIG. 10.

Identification of electrosurgical instruments coupled to the generator and having unique capacitor values may also be performed using a resistance-capacitance combination, as shown in principle in FIG. 10. In this illustration, the signal source 36 produces a positive-going interrogation pulse which is applied to a series resistance 100, the latter being connected, when the instrument is connected to the generator, to an identification capacitor 14 in the instrument so as to form a series R-C combination. The resistance 100 and the capacitor 14 define a R-C time constant dependent upon the value of the capacitor 14. Consequently, the rate of build-up and decay of the voltage on the ID line 64 varies according to the capacitor value. As in previous embodiments, a comparator 46 is used to monitor the voltage on the ID line 64. In this case, a non-zero voltage reference is applied to the reference input of the comparator 46. This reference voltage may be 2.5V (i.e. half the voltage produced by the signal source 36) or somewhat higher in the range of from 0V to the signal source voltage. The waveform diagram of FIG. 11 illustrates, respectively, the interrogation pulse (A), the build-up and decay of the voltage on the identification line 64(B) and the output of the comparator 46 on line 46C. It will be seen that the comparator 46 is used to measure the time delay between the start of the interrogation pulse and the instant during the interrogation pulse at which the voltage on the identification line 64 reaches a predetermined proportion of the potential difference between the two voltage levels outputted by the signal source 36 (measured with respect to either level). A further embodiment may use an analogue-to-digital converter device instead of the comparator; in this case multiple points on the voltage ramp can be digitised and then compared with a predefined curve equation to verify that the expected response is present. Also the rate of change can be computed from the difference in the reading and hence the value of the capacitor is found.

Figure 12:
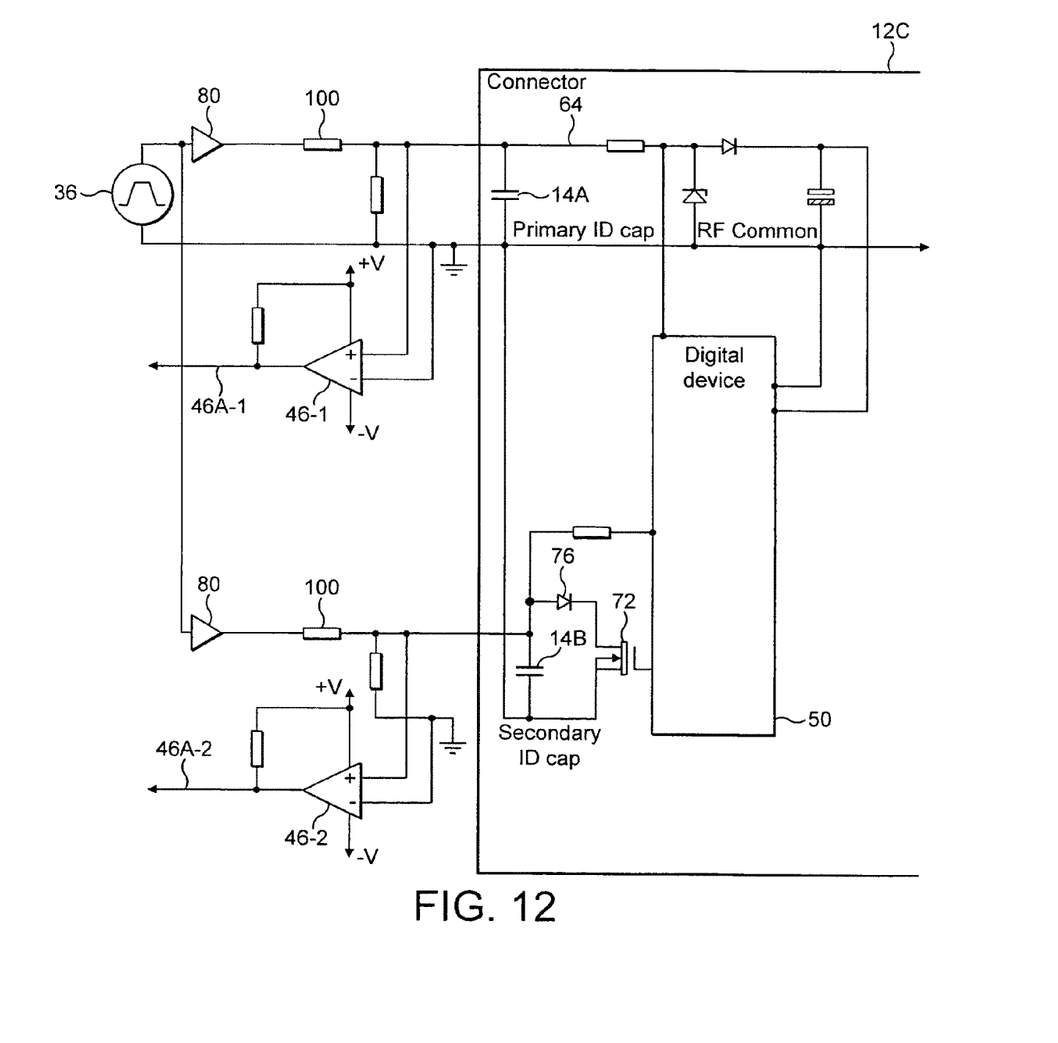
FIG. 12 is a more detailed circuit diagram illustrating yet a further alternative electrosurgical system in accordance with the invention, based upon the principle of the circuitry shown in FIG. 10.

A more detailed circuit diagram of a system using an R-C combination is shown in FIG. 12. This system is similar to that described above in FIG. 5. As in the system of FIG. 5, the signal source 36 normally produces a potential across the first identification capacitor 14A in order to power the digital device 50, the interrogation pulse being a negative-going pulse.

Further variants are possible. For instance, the connection interface may be shifted in any of the illustrated circuits so that, for instance, the comparator 46 or comparators 46-1, 46-2 are contained within the instrument (the "second" unit).

While the invention has been described in connection with what is presently considered to be the most practical and preferred embodiments, it is to be understood that the invention is not to be limited to the disclosed embodiments, but, on the contrary, is intended to cover various modifications and equivalent arrangements included within the spirit and scope of the appended claims.

What is claimed is:

1. An electrosurgical instrument for use in an electrosurgical system, the electrosurgical instrument comprising:
   at least one tissue treatment electrode;
   a mounting portion for detachably securing the electrosurgical instrument to a part of the electrosurgical system that is different from the electrosurgical instrument;
   a first passive electrical circuit component which is used to identify the electrosurgical instrument, the first passive electrical circuit identification component being arranged to form a combination circuit with a second electrical circuit component in a sensing circuit associated with the different part of the electrosurgical system, the first passive electrical circuit identification component having an electrical parameter of a finite non-zero value indicative of the electrosurgical instrument;
   a digital device including a memory, wherein the digital device is not used for the identification of the electrosurgical instrument; and
   a first set of contacts for engaging a second set of contacts on the different part of the electrosurgical system;
   wherein the first set of contacts includes a pair of contacts which are interconnected by the first passive electrical circuit identification component so as to transmit an identification signal to the part of the electrosurgical system that is different from the electrosurgical instrument, and which are also connected to the digital device so that the interconnected pair of contacts serve at least one function of (a) supplying power from the different part of the electrosurgical system to a power supply terminal of the digital device and (b) conveying data from a data output of the digital device to the different part of the electrosurgical system.

2. The electrosurgical instrument according to claim 1, having a second tissue treatment electrode in addition to the at least one tissue treatment electrode, one of the tissue treatment electrodes being coupled to the pair of interconnected contacts.

3. The electrosurgical instrument according to claim 1, wherein the digital device is arranged to be powered via the pair of interconnected contacts and to output data from the digital device's data output in response to detection of an interrogation pulse on the pair of interconnected contacts, the interrogation pulse interrupting a supply of power to the digital device.

4. The electrosurgical instrument according to claim 3, wherein the digital device is arranged to output the data from the digital device's data output after the end of the interrogation pulse.

5. The electrosurgical instrument according to claim 1 further comprising a second passive electrical circuit identification component used to identify the electrosurgical instrument, the second passive electrical circuit identification component being in addition to the first passive electrical circuit identification component, wherein the first set of contacts includes a first pair of contacts and a second pair of contacts, the first passive electrical circuit identification component interconnects the first pair of contacts and the second passive electrical circuit identification component interconnects the second pair of contacts, the digital device is powered via one pair of the first and second pairs of contacts, and the digital device is configured to output data via a contact of a different pair of the first and second pairs of contacts.

6. The electrosurgical instrument according to claim 1 wherein the memory of the digital device is configured to store data including parameters for operating a radio frequency generator provided in the different part of the electrosurgical system.

7. The electrosurgical instrument according to claim 1 further comprising a second passive electrical circuit identification component used to identify the electrosurgical instrument, wherein the first set of contacts includes a first pair of contacts and a second pair of contacts, the first passive electrical circuit identification component interconnects the first pair of contacts and the second passive electrical circuit identification component interconnects the second pair of contacts, and the digital device is configured to (1) receive, from the different part of the electrosurgical system, data via one of the contacts of the second pair of contacts and (2) transmit, to the different part of the electrosurgical system, data via a transistor coupled across the second pair of contacts.

* * * * *